United States Patent [19]
Bates et al.

[11] Patent Number: 5,496,330
[45] Date of Patent: Mar. 5, 1996

[54] SURGICAL EXTRACTOR WITH CLOSELY ANGULARLY SPACED INDIVIDUAL FILAMENTS

[75] Inventors: James S. Bates, Bloomington, Ind.; Hugh A. Tripp, Foxboro, Mass.

[73] Assignee: Boston Scientific Corporation, Natick, Mass.

[21] Appl. No.: 258,121

[22] Filed: Jun. 10, 1994

Related U.S. Application Data

[63] Continuation of Ser. No. 19,551, Feb. 19, 1993, abandoned.
[51] Int. Cl.⁶ .................................................. A61B 19/00
[52] U.S. Cl. .................................. 606/127; 606/113
[58] Field of Search ........................... 606/1, 106, 108, 606/110, 113, 114, 117, 128, 159, 205, 209

[56] References Cited

U.S. PATENT DOCUMENTS

| | | |
|---|---|---|
| 2,943,626 | 7/1960 | Dormia . |
| 3,108,593 | 10/1963 | Glassman . |
| 3,472,230 | 10/1969 | Fogarty . |
| 4,046,149 | 9/1977 | Komiya . |
| 4,046,150 | 9/1977 | Schwartz et al. . |
| 4,203,429 | 5/1980 | Vasilevsky . |
| 4,299,225 | 11/1981 | Glassman . |
| 4,347,846 | 9/1982 | Dormia . |
| 4,590,938 | 5/1986 | Segura et al. . |
| 4,610,662 | 9/1986 | Weikl et al. . |
| 4,611,594 | 9/1986 | Grayhack et al. . |
| 4,616,652 | 10/1986 | Simpson . |
| 4,625,726 | 12/1986 | Duthoy . |
| 4,633,871 | 1/1987 | Shinozuka ............... 606/127 |
| 4,807,626 | 2/1989 | McGirr . |
| 5,098,441 | 3/1992 | Wechler ................ 606/113 |
| 5,176,688 | 1/1993 | Narayan et al. .......... 606/127 |
| 5,190,557 | 3/1993 | Borodulin et al. ........ 606/127 |
| 5,197,968 | 3/1993 | Clement ................. 606/127 |

FOREIGN PATENT DOCUMENTS

| | | | |
|---|---|---|---|
| 0428998 | 5/1991 | European Pat. Off. ..... 606/127 |
| 2428319 | 1/1976 | Germany ............... 606/127 |
| 9222254 | 12/1992 | WIPO .................. 606/114 |

*Primary Examiner*—Stephen C. Pellegrino
*Assistant Examiner*—Glenn Dawson
*Attorney, Agent, or Firm*—Pearson & Pearson

[57] ABSTRACT

A surgical extractor for removing calculi, such as kidney stones and gall stones, from the body. The extractor includes a handle at an proximal end of the extractor with a slider for operation by a physician. At the distal end the extractor includes a plurality of pairs of wires with portions of each pair being formed along the turn of a helix. When a retaining sheath is retracted, the wires, formed of a shape memory material such as stainless steel, expand such that each pair of wires closely assumes a path along a helical turn with individual wires remaining closely adjacent. This use of plural wires for each strand multiples the number of contacts with entrapped calculi and can be provided without any deleterious effect on the reliability or size of the extractor.

35 Claims, 4 Drawing Sheets

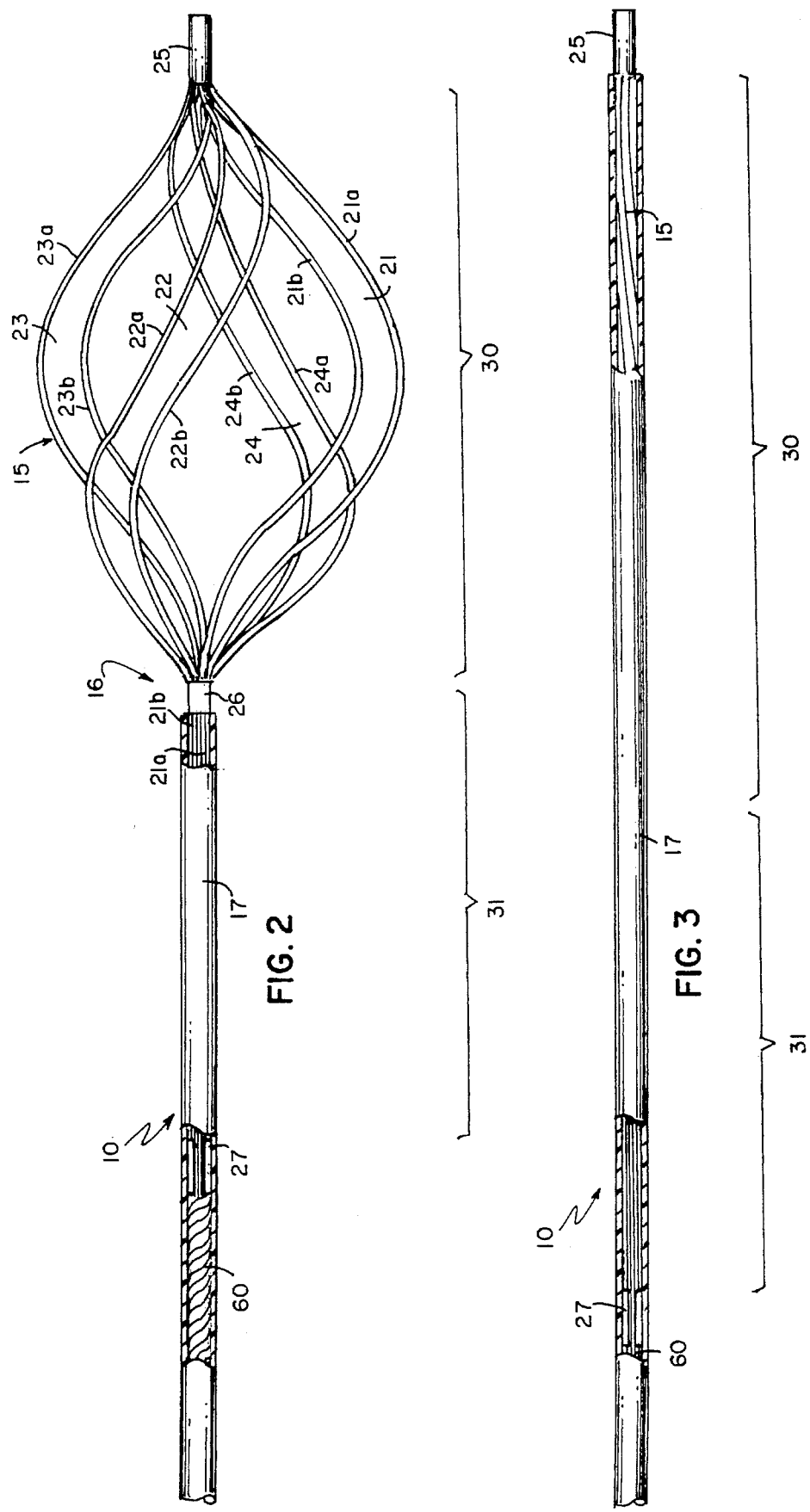

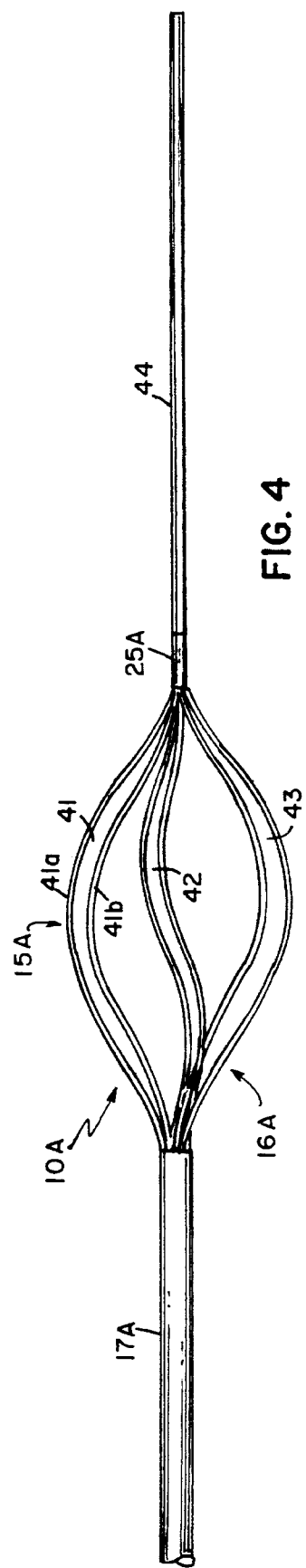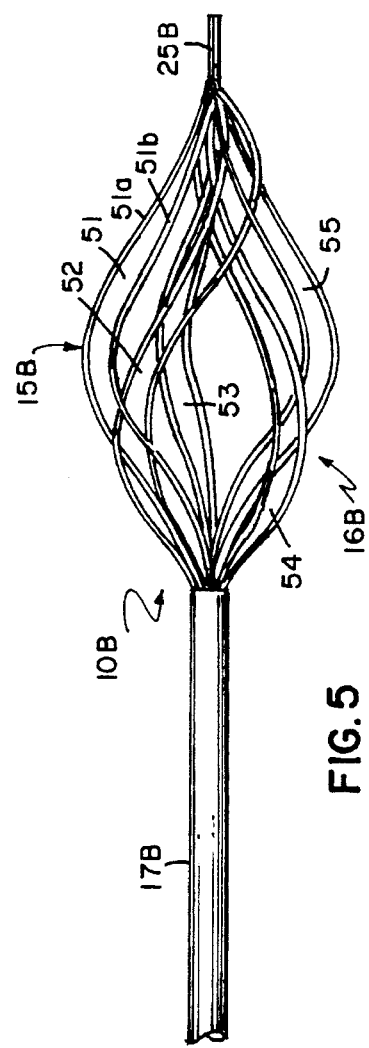

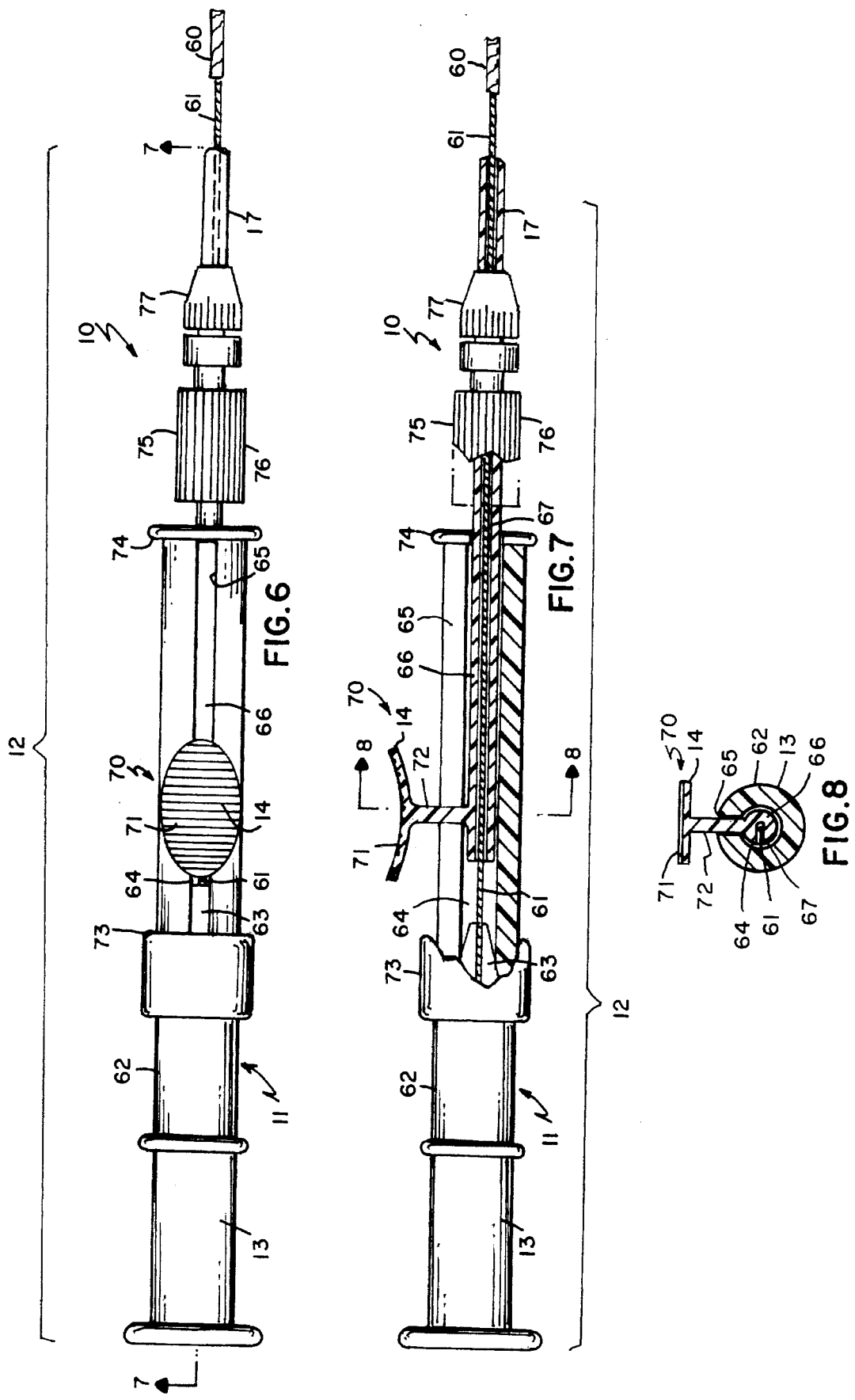

5,496,330

SURGICAL EXTRACTOR WITH CLOSELY ANGULARLY SPACED INDIVIDUAL FILAMENTS

This application is a continuation of U.S. patent application Ser. No. 08/019,551 filed on Feb. 19, 1993 (now abandoned).

BACKGROUND OF THE INVENTION

1. Field of the Invention

This invention generally relates to medical instruments and more specifically to an extractor for removing an object from a body, particularly calculi that can form in the biliary and urinary systems.

2. Description of Related Art

Recently developed medical instruments reduce the invasiveness and potential trauma previously associated with various medical procedures. The removal of calculi in the form of kidney stones, gallstones and the like from the body is one area where this effort is meeting with success. Various instruments now permit the removal of kidney stones and gallstones without the need for major surgery.

Some of these instruments incorporate miniaturized grasping forceps. This invention, however, is directed to an alternative set of instruments that utilize mechanical retrieval baskets as described in the following United States Letters Patent:

4,590,938 (1986) Segura et al
4,611,594 (1986) Grayhack et al
4,625,726 (1986) Duthoy
4,807,626 (1989) McGirr The Segura et al patent discloses a medical retrieval device that can be inserted through the working channel of an endoscope for removing stones and the like from the kidneys or the ureter or biliary duct. It includes a retrieval basket of relatively large diameter that is extendable from the distal end of a sheath and collapsible when withdrawn into the sheath. Outwardly bowed spring strips form the retrieval basket. These strips extend generally axially of the sheath and join at respective distal and proximal ends. The retrieval basket has a generally bulbous form which is relatively stiff due to the spring strip construction and facilitates dislodgement and capture of stones.

The Grayhack et al patent discloses another retrieval basket that is useful during the removal and/or destruction of calculi. A smooth outer tubular sheath overlies and contains a stranded wire cable terminating in a protective tip at the working or distal end of the device. When the cable is extended distally, the spring wire strands at the working end of the cable expand to form a retrieval basket. The distal end of this device additionally includes an expandable distal portion for protecting surrounding tissue during withdrawal of the device and calculi.

The Duthoy patent discloses an extraction device that includes a retrieval basket formed from a plurality of wires spaced about and outwardly from an imaginary extension of the center line of a hollow cable. A filiform extends distally from the distal end of the retrieval basket to extend past a stone and to allow the basket to be threaded around and onto the calculi.

The McGirr patent discloses an extractor included a self-closing retrieval basket at the distal end of a catheter with a flexible control line for opening the basket from the proximal end of the catheter. The basket assumes a normal position wherein it is in a compact closed form. Pulling on the control line flexes the strips to open the basket. When the control line is released, the strips relax and surround the calculi or object being removed.

These and other surgical extractors fusing retrieval baskets have certain common characteristics. Each retrieval basket comprises a plurality of strands in the form of individual strips or wires substantially equiangularly spaced about the retrieval basket. In some retrieval baskets the strands are formed along substantially straight lines when the basket is in a compact form; in others, the individual strands extend along a generally helical path. Each instrument includes a plurality of three or more strands. However, the overall size or diameter of an extractor and ancillary equipment, such as an endoscopic device, can impose upper limits on that plurality. For example, an instrument having a sheath outer diameter of 3.0 Fr can incorporate up to 6 wires each having a diameter 0.008 inches in the prior art.

Additional wires could be advantageous because increasing the number of wires increases the number of contacts between the basket and any entrapped calculi. However, the overall size limitation means that additional wires can be incorporated only by decreasing their diameters. As the individual diameters reduce, they become weaker. Moreover the individual wires are generally equiangularly spaced, so the additional wires reduce the angular spacing between adjacent wires. This can complicate the manipulation of an expanded retrieval basket onto calculi. Wires of reduced diameter can also limit any radially acting, dilating force that the wires exert against surrounding tissue when the retrieval basket expands. In some applications the retrieval basket may not fully open. This attribute can reduce the opening between adjacent wires and make it more difficult to entrap calculi. Even prior art extractors with larger single wires can fail to expand fully with the same result.

SUMMARY

Therefore it is an object of this invention to provide a surgical extractor that increases the reliability of retaining calculi in a retrieval basket.

Another object of this invention is to provide a surgical extractor that increases the number of contact points with calculi in a retrieval basket without increasing the overall size of the instrument.

Still another object of this invention is to provide a surgical extractor that increases the number of contact points with entrapped calculi without reducing the dilating force that the extractor can apply to surrounding tissue.

Yet another object of this invention is to provide a surgical extractor that increases the number of contacts with entrapped calculi in an extractor and that opens fully when expanded.

Yet still another object of this invention is to provide a surgical extractor that increases the number of contacts with entrapped calculi in an extractor that is readily manufactured.

Still yet another object of this invention is to provide a surgical extractor that increases the number of contact points with entrapped calculi and requires substantially the same level of physician dexterity as required by prior art extractors having a fewer number of such contact points.

In accordance with this invention a surgical extractor for removing an object from a body includes a plurality of prestressed strands that are normally encased in a sheath and wrapped in a helical form. The displacement of the sheath from the prestressed strands enables the strands to form a basket for retrieving the object. Each of the strands comprises a plurality of individual filaments.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 2 is a enlarged plan view of the distal end of the extractor shown in FIG. 1;

FIG. 3 is an enlarged view, partially in cross section, of the distal end of the extractor shown in FIGS. 1 and 2 in a compact form;

FIG. 4 depicts the distal end of a surgical extractor incorporating a different embodiment of a retrieval basket;

FIG. 5 depicts the distal end of another surgical extractor with still a different retrieval basket;

FIG. 6 is an enlarged plan view of the handle at the proximal end of the extractor shown in FIG. 1; and FIG. 7 is another view, partially in section, taken along lines 7—7 in FIG. 6; and FIG. 8 is a cross sectional view taken along lines 8—8 in FIG. 7.

DESCRIPTION OF ILLUSTRATIVE EMBODIMENTS

Figure 1:
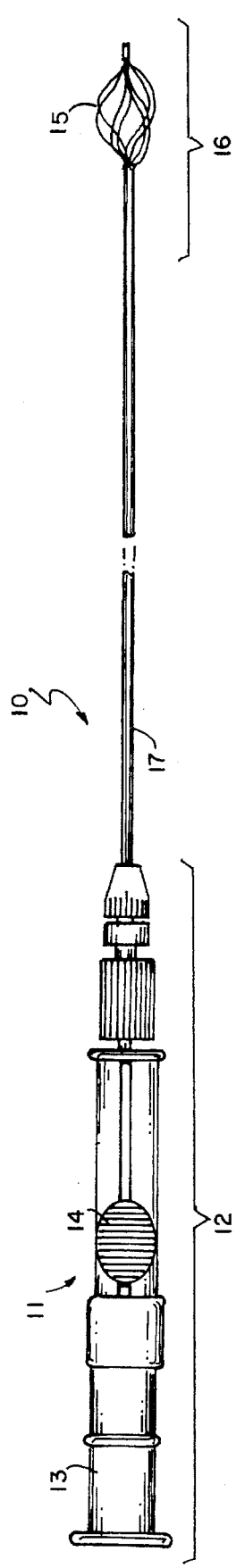
FIG. 1 is a plan view of a surgical extractor constructed in accordance with this invention with a handle at a proximal end and an expanded retrieval basket at a distal end.

FIG. 1 depicts one embodiment of a surgical extractor 10 constructed in accordance with this invention. The surgical extractor 10 includes a handle 11 at a proximal end 12 having a base 13 and a slider 14. A physician can grasp the base 13 in the palm of his or her hand and manipulate the slider 14 with his or her thumb. A retrieval basket 15 constructed in accordance with this invention is located at the distal end 16 of the extractor 10. A sheath 17 overlies an intermediate supporting structure between the handle 12 and the retrieval basket 15.

As shown in FIG. 1 the slider 14 is located at a proximal position. When the slider 14 advances to a distal position, that is to the right in FIGS. 1 and 2, the sheath 17 advances to compact and cover the retrieval basket 15 as shown in FIG. 3. The sheath 17 typically comprises a polyimide tube or a tube of another material that exhibits the radial flexibility, axial stiffness, biocompatability and hoop strength of a polyimide tube.

FIG. 2 depicts the distal end 16 of the surgical extractor 10 in an enlarged form and specifically discloses a substitute for a prior art four-wire retrieval basket. The retrieval basket comprises a plurality of four prestressed strands 21, 22, 23 and 24. In accordance with this invention, each of these strands comprises a plurality of individual wires. The strand 21, for example, comprises wires 21a and 21b; the strand 22, wires 22a and 22b; the strand 23, wires 23a and 23b and the strand 24, wires 24a and 24b. These wires will be made from stainless steel or some other shape memory material.

A cap 25 captures distal ends of all the wires 21a through 24b by soldering the wires in the cap 25, by swaging or by some other method. A sleeve 26 at the proximal end of the basket 25 encircles and is affixed to the wires. The cap 25 and sleeve 26 thereby define the axial extent of the retrieval basket 15 in which the individual wires are prestressed or preformed to the helical expanded shape show in FIGS. 1 and 2. Portions of the individual wires, such as wires 21a and 21b, extend proximally of the sleeve 26 to a connector 27 inside the sheath 17. These portions extend essentially axially between sleeve 26 and a connector 27 and within the sheath 17.

Consequently, the structure shown in FIG. 2 produces a retrieval basket 15 in a distal portion 30 of the wires 21a through 24b and a proximal portion 31 intermediate the sleeve 26 and connector 27. Each of the wires lies in parallel in the proximal wire portion 31, and each of the: wires is independent in the distal portion 30. Therefore, the distal end 16 of the extractor 10 remains radially flexible and, by virtue of the sheath 17, axially stiff to facilitate placement of the extractor 10. The combination of radial flexibility and axial stiffness is particularly important when the extractor 10 has the form shown in FIG. 3 with the sheath 17 advanced distally to the cap 25.

More specifically, a physician will introduce the extractor 10 with its distal end 16 in the form shown in FIG. 3. In this form the sheath 17 retains the distal wire portion 30 in its compact form and stresses the individual wires. When the extractor 10 is positioned proximate to calculi to be retrieved, the physician uses the slider 14 in FIG. 1 to retract the sheath 17 and expose the wires in the distal wire portion 30. With the constraint of sheath 17 removed, the wires return to their original shape as shown in FIG. 2 thereby to dilate surrounding tissue and to provide a structure that can be manipulated over the calculi. Once the physician has moved calculi into the retrieval basket 15 defined by the strands 21 through 24, the physician advances the sheath 17 distally and reduces the volume of the retrieval basket 15 until it contacts the entrapped calculi. Then the physician withdraws the extractor 10 with the entrapped calculi.

During manufacture of the specific embodiment of FIG. 2, eight individual wires 21a through 24b are collected together. The distal ends of the wires are soldered or swaged into the cap 25. The wires are separated into pairs corresponding to the strands 21 through 24. Each pair is then formed onto a four-part helix former. Although the wires in a strand, such as wires 21a and 21b associated with strand 21, are formed as a pair of a single strand or thread, the wires are not twisted. Consequently, each of the strands 21 through 24 will be equiangularly spaced, by approximately 90°, but individual wires, such as wires 21a and 21b of a strand, such as strand 21, will be closely angularly spaced. A typical close angular spacing will produce a separation of the wires in a set, such as wires 21a and 21b, by a distance in the range from 0 to 0.5 mm or so.

The increase in the number of wires does not reduce the openings between adjacent strands appreciably, so the effort for moving the retrieval basket 15 over calculi is about the same as required to position a prior art four-strand basket. The sleeve 26 provides a confining force that allows the proximal portion 31 of the wires to lie in a substantially parallel entrusted relationship between the sleeve 26 and connector 27. The manufacturing process also prestressed the individual wires 21a through 25b into the helical form shown in FIG. 2.

The use of multiple wires for a given strand, such as wires 21a and 21b in strand 21, increases the number of contact points with any entrapped calculi. In FIG. 2, for example, eight wires will contact the calculi rather than four. Moreover, the close equiangular spacing of adjacent wires in a given strand also permits the wires collectively to accommodate any surface unevenness of such calculi surfaces to further increase the reliability with which the retrieval basket 15 entraps calculi.

Further, the increase in the number of wires, such as doubling the wires from four to eight in FIG. 2, occurs without increasing the overall size of the sheath 17 or reducing the strength of the retrieval basket 15. For example, it is possible to replace four individual wires having a diameter of 0.008" in a sheath 17 with an outside diameter of 3.0 Fr with eight wires having a diameter of 0.006" due to the change in packing efficiency without a concomitant reduction in the diameter. Thus, for a given material, the collective strength of the retrieval basket 15 and of the strands 21 through 24 can increase by as much as 50% over a single-filament strand of the prior art.

When the sheath 17 moves from the position shown in FIG. 3 to the position shown in FIG. 2 and releases the retrieval basket 15, the retrieval basket 15 can exert the same or a greater dilating force on surrounding tissue as produced by a corresponding prior art device with half of the wires. Thus, the reduction in the wire size and the doubling of the number of contacts with entrapped calculi occurs without affecting the overall strength and reliability of the extractor 10.

FIG. 4 depicts an alternative embodiment of a retrieval basket 15A and sheath 17A at a distal end 16A of the extractor 10A. In this particular embodiment, the retrieval basket 15A comprises three strands 41, 42 and 43. Each strand, again, includes a pair of wires or filaments. For example, the strand 41 includes wires 41a and 41b. A cap 25A captures the distal end of the strands 41, 42 and 43 and another sleeve connector. A sleeve, corresponding to sleeve 26, defines the proximal end of the retrieval basket 15A. In this particular embodiment the strands 41, 42 and 43 would be angularly spaced by about 120°.

In this particular embodiment, the sleeve connector 25A also carries a filiform 44 that extends distally from the retrieval basket 15A. Such filiforms are know in the art. FIG. 4 illustrates the use of a filiform in appropriate circumstances; a filiform can be included as an element in any embodiment of this invention.

FIG. 5 depicts another embodiment of a surgical extractor 10B that includes a retrieval basket 15B at a distal end 16B and a sheath 17B. In this particular embodiment the retrieval basket 15A comprises five substantially equiangularly spaced strands 51 though 55. Each strand comprises a pair of wires or filaments, such as wires 51a and 51b that form strand 51, and forms a portion of a turn of a helix. An end cap 25B retains the distal ends of the wires that form the strands 51 through 55.

AS previously indicated with respect to FIG. 1, the sheath 17 extends between the handle 11 and the distal end 16 and contains an interconnecting link that allows the slider 14 to move the sheath 17 relative to the distal end 16. This link comprises a radially flexible stainless steel cable 60 that is shown at its distal end in FIGS. 2 and 3, and at its proximal end in FIGS. 6 and 7. The sheath 17 retains the cable 60 on its axis.

Now referring to FIGS. 6 through 8, the proximal end of the cable 60 attaches to a rod 61 by swaging, soldering or other method. The rod 61 extends proximally into the handle 11. More specifically, the handle base 13 includes a hollowed handle portion 62 with an internal boss or receptacle 63 that receives the proximal end of the rod 61. Typically the proximal end of the rod 61 will be affixed in the receptacle 63 by an adhesive, ultrasonic or other fastening technique. Consequently, the rod 61, the cable 60 and the basket 15 are fixed spatially with respect to the handle 11.

The slider 14 rides in an axially extending chamber 64 within the base 13 formed with a radially extending slot 65. The slider 14 comprises a cylindrical, elongated body 66 that has a radial passageway 67 for allowing the cylindrical body 66 to slide axially and freely in the chamber 64 with respect to the base 13 and the rod 61.

A thumb actuator 70 includes a thumb pad 71 and radial arm 72 that are molded integrally with and extend radially from the cylindrical body 66. The arm 72 extends through the slot 65 and is therefore slidable along the axis of the extractor 10 between distal and proximal positions. In this particular embodiment the base portion 11 includes radially extending bosses 73 and 74 that define the proximal and distal terminations of the slot 65 respectively. The slider then moves between a proximal position, defined when the arm 72 reaches the boss 73, and a distal position defined when the arm 72 reaches the boss 74.

The distal end of the cylindrical body 66 supports a Luer-lock fitting 75. A first component or base 76 attaches to the cylindrical body 66 and includes an axially extending aperture that allows the rod 61 to pass through the fitting 75. A detachable component 77 carries the sheath 17. Consequently, as a physician moves the thumb actuator pad 71 between proximal and distal positions, the slider 14 and the sheath 17 move relative to the rod 61, the cable 60 and the retrieval basked 15 (FIG. 1). Further as the thumb pad 71 moves toward the distal position, the distal end of the sheath 17, as shown in FIGS. 2 and 3, advances over and compacts the strands 21 through 24 of the retrieval basket 15 due to the axial stiffness and hoop strength of a polyimide tube or tube of similar material.

Therefore, each embodiment disclosed in FIGS. 1 through 8 provides an extractor that meets the various objects of this invention. The extractor requires essentially the degree of dexterity as would be involved with a prior art extractor. In each embodiment the use of strands having multiple, closely adjacent, independent wires formed to be closely adjacent increases the number of contact points with an entrapped calculi without requiring a concomitant increase in the size of the overlying sheath or in the difficulty placing the retrieval basket over calculi. Thus the extractor with multiple wire strands does not subject patient to any increase or trauma during its introduction into the body. Moreover, this is accomplished without affecting the strength and reliability of the retrieval basket.

This invention has been described with respect to specific embodiments constructed with specific materials. Other materials can be substituted for various components. The interconnecting structure between the retrieval basket at the distal end of the extractor and the handle=can be modified. Different numbers of strands and different numbers of wires or filaments in a strand may be incorporated in an extractor. It also will be apparent that many other modifications can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. In a surgical extractor for removing an object from a body including a plurality of threads normally encased in a sheath and wrapped in a helical form whereupon displacement of a portion of the threads from the sheath enables the portions of the threads to become relatively widely angularly spaced to form a basket with distal and proximal ends for retrieving an object, the improvement wherein each thread comprises a plurality of individual filaments that are closely angularly spaced throughout the length of the basket relative to the spacing of adjacent threads upon the displacement of the portions of the threads from the sheath.

2. A surgical extractor as recited in claim 1 wherein said filaments are formed of a shape memory material.

3. A surgical extractor as recited in claim 2 wherein the shape memory material is stainless steel.

4. A surgical extractor as recited in claim 3 wherein each thread comprises a pair of said filaments.

5. A surgical extractor as recited in claim 4 wherein said plurality of threads is in the range of 3 to 5.

6. A surgical extractor as recited in claim 5 wherein each of said filaments in each of said pairs are untwisted.

7. A surgical extractor as recited in claim 1 wherein at least one of the threads comprises a pair of filaments.

8. A surgical extractor as recited in claim 1 wherein said plurality of said threads is in the range of 3 to 5.

9. A surgical extractor as recited in claim 8 wherein each of the threads comprises a pair of filaments.

10. A surgical extractor as recited in claim 9 wherein each of said filaments in each of said pairs are untwisted.

11. A surgical extractor as recited in claim 1 wherein each of said filaments is untwisted.

12. A surgical extractor as recited in claim 11 wherein each thread comprises a pair of filaments.

13. A surgical extractor for removing an object from a body comprising:
  A. handle means extending along an axis at a proximal portion of said extractor for operating said extractor, said handle means having base means for being grasped by a physician and slider means for reciprocating along the axis with respect to said base means,
  B. basket forming means connected to said base means for forming a basket distally of said handle means, said basket forming means including a plurality of sets of filaments being helically wound with each of said sets of filaments constituting a turn in a helix, and each of said sets of filaments comprising a plurality of individual, closely angularly spaced filaments that are prestressed in a distal portion thereof for forming an enlarged basket, and
  C. sheath means connected to said slider means and axially displaceable between first and second positions with respect to said basket forming means whereby said sheath means retains said filaments in a compact form within said sheath means in a first position and exposes the distal portion of said basket forming means in the second position thereby to enable said prestressed filaments to form the enlarged basket with each of said sets of filaments throughout the length of said enlarged basket being relatively widely, angularly spaced from adjacent ones of said sets of filaments and said filaments in one of said sets remaining closely angularly spaced throughout the length of the basket relative to the angular spacing of adjacent sets of filaments.

14. A surgical extractor as recited in claim 13 wherein said filaments are formed of a shape memory material.

15. A surgical extractor as recited in claim 14 wherein the shape memory material is stainless steel.

16. A surgical extractor as recited in claim 15 wherein each of said sets comprises a pair of filaments.

17. A surgical extractor as recited in claim 16 wherein said plurality of said sets is in the range of 3 to 5.

18. A surgical extractor as recited in claim 17 wherein each of said filaments in a pair is untwisted.

19. A surgical extractor as recited in claim 16 wherein each of said filaments in a pair is untwisted.

20. A surgical extractor as recited in claim 13 wherein each of said sets comprises a pair of filaments.

21. A surgical extractor as recited in claim 20 wherein said handle base means and said handle slider means are formed of molded plastic.

22. A surgical extractor as recited in claim 13 wherein said plurality of said sets is in the range of 3 to 5.

23. A surgical extractor as recited in claim 22 wherein each of said sets comprises a pair of filaments.

24. A surgical extractor as recited in claim 23 wherein each of said filaments in a pair is untwisted.

25. A surgical extractor as recited in claim 13 additionally comprising radially flexible, axially stiff support means attached intermediate said handle base means and said basket forming means and lying within said sheath means wherein said filaments additionally have a proximal portion that attaches to a distal end of said support means and said basket forming means additionally includes means at opposite ends of said distal portion for binding said filaments and limiting the axial extent of said enlarged basket.

26. A surgical extractor as recited in claim 25 wherein said binding means includes a filiform extending distally of said distal portion.

27. A surgical extractor as recited in claim 25 wherein each of said set comprises a pair of said filaments.

28. A surgical extractor as recited in claim 27 wherein said plurality of set is in the range of 3 to 5.

29. A surgical extractor as recited in claim 25 wherein said filaments and support means are formed of stainless steel.

30. A surgical extractor as recited in claim 29 wherein said sheath comprises a polyimide tube that overlies said support means and said plurality of said filaments.

31. A surgical extractor as recited in claim 25 wherein said handle base means includes means for engaging said slider means thereby to limit the axial motion of said slider means and wherein said support means connects to said handle base means.

32. A surgical extractor as recited in claim 31 wherein said support means and said filaments are formed of stainless steel and said sheath is formed of polyimide.

33. A surgical extractor for removing objects from a body comprising:
  A. a molded plastic, partially hollowed base extending axially,
  B. support means including a solid stainless steel radially flexible, axially stiff rod attached to said base and extending distally therefrom, a stainless steel cable extending distally from said rod and means for connecting said rod and said cable together axially,
  C. a plurality of strands comprising a plurality of pairs of spaced stainless steel wires attached to the distal end of said cable and including means for defining proximal and distal portions of said wires, said strands in said distal portion being formed to conform to a helix having a greater diameter than said proximal portion and each of said strands being equiangularly spaced with individual wires in each of said strands being closely angularly spaced,
  D. a plastic slider captured in said base for limited axial movement relative thereto between distal and proximal positions, and E. a polyimide sheath of a given diameter having a proximal end attached to said slider for overlying said support means and said strands, said slider, in its distal position, locating said sheath coextensively with said distal portion of said strands thereby to compact and retain said strands at substantially the given diameter and, in its proximal position, retracting said sheath to release said strands to form an enlarged retrieval basket for entrapping the object intermediate proximal and distal ends of said basket with adjacent ones of said strands extending between the proximal and distal ends of the basket being relatively widely angularly spaced and individual wires in at least one of said strands being relatively closely angularly spaced between the proximal and distal ends of the basket.

34. A surgical extractor as recited in claim 33 wherein said surgical extractor additionally includes a filiform extending distally of said strands for facilitating the steering of said extractor to the object.

35. A surgical extractor as recited in claim 34 wherein said plurality of said strands is in the range of three to five strands.

* * * * *